United States Patent
Ren et al.

[11] Patent Number: 6,045,547
[45] Date of Patent: Apr. 4, 2000

[54] SEMI-CONTINUOUS CO-EXTRUDED CATHETER SHAFT

[75] Inventors: Brooke Q. Ren, Champlin, Minn.; Paul Miller, Galway, Ireland

[73] Assignee: SciMed Life Systems, Inc., Maple Grove, Minn.

[21] Appl. No.: 09/094,889

[22] Filed: Jun. 15, 1998

[51] Int. Cl.$^7$ .................................................. A61M 25/00
[52] U.S. Cl. ........................ 604/525; 604/264; 604/527
[58] Field of Search ................................ 604/525, 524, 604/523, 264, 526, 527

[56] References Cited

U.S. PATENT DOCUMENTS

| | | | |
|---|---|---|---|
| 4,495,134 | 1/1985 | Ouchi et al. | 264/516 |
| 4,753,765 | 6/1988 | Pande | 264/149 |
| 4,782,834 | 11/1988 | Maguire et al. | 128/344 |
| 5,061,257 | 10/1991 | Martinez et al. | 604/282 |
| 5,470,322 | 11/1995 | Horzewski et al. | 604/280 |
| 5,569,220 | 10/1996 | Webster, Jr. | 604/282 |
| 5,725,513 | 3/1998 | Ju et al. | 604/280 |
| 5,782,809 | 7/1998 | Umeno et al. | 604/280 |
| 5,782,811 | 7/1998 | Samson et al. | 604/282 |
| 5,792,124 | 8/1998 | Horrigan et al. | 604/525 |
| 5,851,203 | 12/1998 | van Muiden | 604/525 |

FOREIGN PATENT DOCUMENTS

| | | |
|---|---|---|
| 0 631 791 A1 | 1/1995 | European Pat. Off. |
| 0 808 637 A1 | 11/1997 | European Pat. Off. |
| WO 96/38194 | 12/1996 | WIPO |
| WO 98/44979 | 10/1998 | WIPO |

*Primary Examiner*—John D. Yasko
*Attorney, Agent, or Firm*—Crompton, Seager & Tufte, LLC

[57] ABSTRACT

A multi-layer catheter tube section providing gradually increasing flexibility. One catheter tube section has a first, inner layer formed of a flexible material and a second, outer layer formed of a stiffer material. The outer layer tapers distally, having decreasing layer thickness with increasing distal position. The decreasing wall thickness provides a decreasing stiffness contribution which imparts increasing flexibility to the catheter portions having a smaller outer layer. The tube sections can be joined end to end to form longer catheter regions having a greater number of gradual flexibility changes.

14 Claims, 1 Drawing Sheet

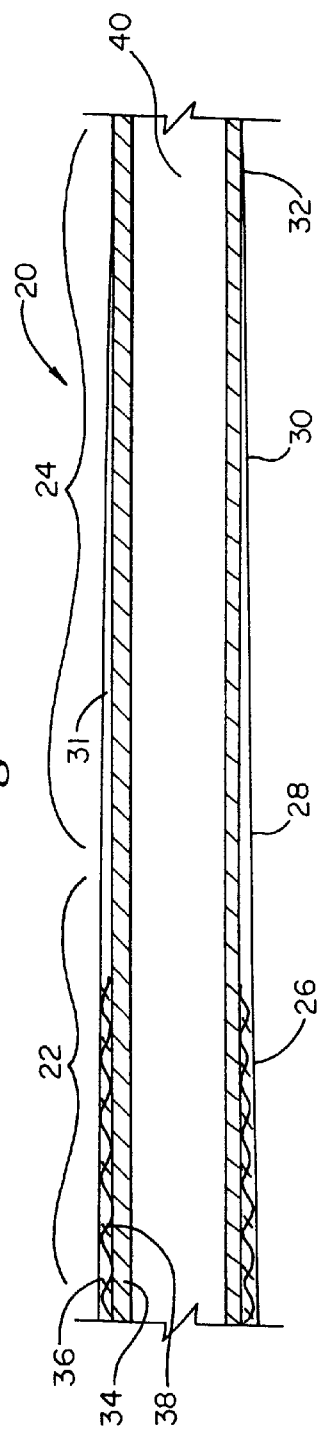
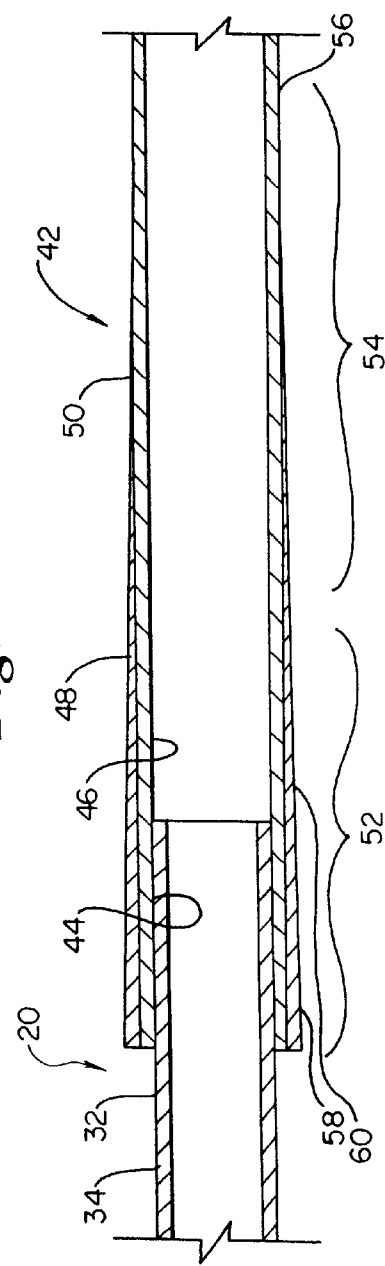
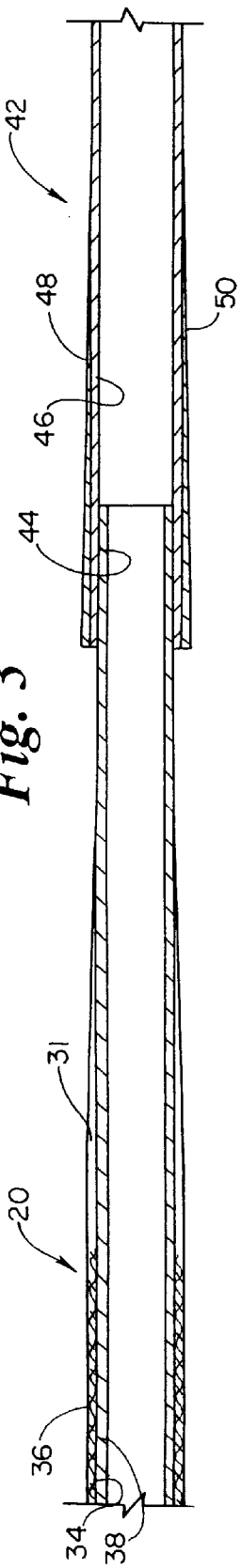

SEMI-CONTINUOUS CO-EXTRUDED CATHETER SHAFT

FIELD OF THE INVENTION

The present application is related generally to medical catheters. Specifically, the present invention is related to intravascular catheters having controlled gradual increasing flexibility toward the distal end.

BACKGROUND OF THE INVENTION

Catheters are used in medical procedures for diagnostic and therapeutic purposes. Diagnostic cardiac catheters are used to infuse radiopaque contrast media into heart blood vessels to allow visualization under fluoroscopy. Therapeutic cardiac balloon catheters are used in angioplasty procedures to dilatate narrowed coronary blood vessels. Guide catheters are often used as conduits, to guide diagnostic and therapeutic catheters to a target position in a vessel.

Cardiac catheters are often inserted through an incision in the femoral artery near the groin, advanced through the femoral artery, advanced over the aortic arch, and inserted into a coronary artery ostium. Once the catheter distal tip is within the ostium, it can be further advanced into smaller branch arteries, until the target site in a coronary artery is reached.

Advancing a catheter along the above described path requires pushability, torqueability and flexibility in differing degrees in different regions of the catheter shaft. In particular, the proximal region of the catheter shaft will ultimately lie within the femoral artery, where flexibility is not as important as the pushability and torqueability required to maneuver the more distal regions of the catheter disposed within the coronary arteries. The intermediate regions between the proximal and distal regions may be required to bend over the aortic arch, where some greater degree of flexibility is required. The distal region of the catheter requires a high degree of flexibility to maneuver through the tortuous path through curved and ever smaller branch arteries.

The intermediate region thus requires more flexibility than the proximal region, and the distal region requires more flexibility than the intermediate region. This increasing flexibility has been provided for in catheters by making different catheter regions from tubular materials having different flexibilities. Individual tubes of appropriate length are joined at their respective ends to form a longer tube having the different flexibility regions. A more rigid tube may be joined at its distal end to a more flexible tube. Where the tubes are joined, there is a discontinuity or sudden change in flexibility. A gradual change in flexibility would be preferable as being less prone to kinking and better matched to the gradual increased need for flexibility over the catheter length.

What has not been heretofore provided and what would be desirable is a catheter tube having improved, gradually distally increasing flexibility. What would be desirable is a catheter tube having controlled flexibility increases over a substantial length of the catheter.

SUMMARY OF THE INVENTION

The present invention includes multi-layer catheter tubes having improved transitions in flexibility. Gradually increasing tube flexibility can be obtained by extruding an outer tube layer over a more flexible inner tube layer, and decreasing the thickness of the outer layer with increasing distal position. The thickness of the outer layer can be tapered down over several inches such that the stiffness contribution of the outer layer is reduced gradually, thereby gradually increasing tube flexibility. The stiffness of the outer tube layer material can be selected to give a preferred resultant stiffness in combination with the inner tube layer.

One catheter tube section has a first, inner tube or layer having a wall thickness and formed of a material having a first flexibility. A second, outer layer is disposed over the first tube, with the second layer material having a second flexibility less than the flexibility of the first tube material. The second layer has a taper with distally decreasing wall thickness such that the catheter tube section has distally increasing flexibility. The taper length and region of gradually increasing flexibility is selected for a particular application but can extend over a substantial portion of the catheter tube.

The outer tube can have a region of substantially constant wall thickness followed distally by a taper which terminates, leaving the inner tube with no outer layer. One catheter tube section has a stiffening sleeve between the inner and outer tubes, with the stiffening sleeve disposed in a proximal region of the catheter tube such that the distal termination of the stiffening sleeve provides another increase in flexibility. The stiffening sleeve preferably terminates distally proximal of the outer tube taper. A preferred stiffening sleeve is formed of a metal wire braid.

Catheter tube sections, some or all including a tapered outer layer of less flexibility than the inner layer, can be joined together to form longer catheter sections having an even greater number of flexibility transitions. The tube sections can be joined by abutting and bonding the sections or by inserting the end of one tube section into the end of another tube section, preferably followed by adhesive or thermal bonding. The materials used to form the proximal and distal tube sections preferably have increasing flexibility with increasingly distal position. In one embodiment, the combined inner and outer layers in the more distal tube section are more flexible than the inner layer alone in the more proximal tube section. By combining several tube sections together, the change in materials, diameter, wall thickness and tapering of the outer layer wall thickness can combine to provide a large number of increasingly flexible tube portions over the length of a catheter.

Tube sections having a tapered outer layer are formed in one method by extruding the inner tube from one extruder and passing the inner tube through a second extruder in line with the first extruder, where the outer layer is extruded over the inner layer and gradually decreased in wall thickness. The inner layer can be extruded over a wire or mandrel to provide support and increased control over the inside diameter of the tube. In another method, the first tube is passed through the same extruder a second time, with the extruder having a second material loaded for the second pass.

BRIEF DESCRIPTION OF THE DRAWINGS

FIG. 1 is a fragmentary, longitudinal cross-sectional view of a first multi-layer catheter tube section having an inner layer, a tapered outer layer, and a stiffening sleeve therebetween;

FIG. 2 is a fragmentary, longitudinal cross-sectional view of a second multi-layer catheter tube section having the first tube section of FIG. 1 joined to the second tube section, the second section having an inner layer and a tapered outer layer; and FIG. 3 is a fragmentary, longitudinal cross-sectional view of a multi-layer catheter having multiple tube sections joined together, each with an inner layer and tapered outer layer.

DETAILED DESCRIPTION OF THE PREFERRED EMBODIMENTS

FIG. 1 illustrates a first catheter tube section 20 having a proximal region 22, a distal region 24, and a lumen 40 therethrough. Proximal region 22 includes a proximal portion 26 and a distal portion 28. Distal region 24 includes a proximal portion 30 and a distal portion 32. The proximal and distal descriptors are used herein to refer to relative positions on both the catheter as a whole and on the individual tubes or layers making up the catheter.

First catheter tube section 20 is formed of an inner layer or tube 34 having an outer layer or tube 36 disposed thereabout. In the embodiment of FIG. 1, a stiffening sleeve 38 is disposed between inner layer 34 and outer layer 36. Stiffening sleeve is formed of a wire braid in one preferred embodiment and a wire helix in another embodiment. Alternatively, a polymer braid or helix could be utilized. Inner layer 34 is preferably formed of a first material and outer layer 36 is preferably formed of a second material different from the first material. By different material, it is meant any polymer having a different stiffness or flexibility (flexural modulus) when extruded relative to the other polymer. Thus, for example, both materials could be a polyether block amide (PEBAX), but of different durometer. The first, inner material is preferably more flexible than the second, outer material. The distal portion 32 of distal region 24 thus is more flexible than the more proximal tube areas having the flexible material surrounded by more rigid material. The different material used may be any compatible polymers differing in stiffness when extruded.

Distal region 24 includes a taper 31 in outer tube or layer 36, indicated by a decreasing layer or wall thickness over distal region proximal portion 30. Taper 31 is illustrated terminating distally, such that distal region distal portion 32 does not have outer layer 36 disposed about inner layer 34. In a preferred embodiment, taper 31 is in the range of about 1 to 5 inches in length for "single operator exchange" catheters and in the range of about 1 to 20 inches in length for "over the wire catheters." In a preferred embodiment, inner layer 34 has a substantially constant thickness over its length, while outer layer 36 has a substantially constant thickness proximal of taper 31.

Outer layer 36, being formed of a more rigid material than the material of inner layer 34 and disposed about inner layer 34, imparts added rigidity to the tube section, the rigidity resulting from the greater outer layer thickness and outer layer material. Stiffening sleeve 38 also adds rigidity to the catheter tube region containing it.

In the embodiment illustrated, flexibility increases distally over the catheter tube length. The increase is gradual in some parts and step wise in other parts. Beginning with proximal region 22, the least flexibility is found in proximal portion 26, as it has inner layer 34, surrounded by stiffening sleeve 38, surrounded by outer layer 36, where outer layer 36 is formed of a more rigid material than inner layer 34 and preferably has a maximum and constant thickness over the length of proximal region proximal portion 26. Proceeding distally, flexibility increases in proximal region distal portion 28, as distal portion 28 does not contain stiffening sleeve 38. Distal region 24 has taper 31 within, with the thickness of outer layer 36 decreasing distally, thereby increasing the flexibility of multi-layer tube section 20 within, as there is less rigid material disposed about inner layer 34. Distal region distal portion 32 is still more flexible, as outer layer 36 has terminated, leaving only flexible inner layer 34. The catheter tube section illustrated thus has at least four different flexibility portions over its length, with flexibility smoothly increasing distally over the length of taper 31.

Referring now to FIG. 2, a second catheter tube section 42 is illustrated, joined distally at 44 to first section inner layer 34. Second catheter tube section 42 includes an inner layer or tube 46 and an outer layer or tube 48. Outer layer 48 includes a proximal region 52 and a distal region 54, with proximal region 52 having a proximal portion 58 where first tube section 20 is joined to second tube section 42, and a distal portion 60. Outer layer 48 includes a taper 50 in distal region 54. Outer layer 48 terminates, leaving only inner layer 46 extending through a distal portion 56 of distal region 54.

In a preferred embodiment, outer layer 48 is formed of a more rigid material than inner layer 46, and inner and outer layers 46 and 48 together are more rigid than inner layer 34 in first catheter tube distal region distal portion 32. Flexibility thus preferably increases from first catheter tube section 20 to second tube section 42. A smooth appearance near the junction of two joined tube sections is provided in one embodiment by abutting and bonding the tubes rather than overlapping them. Flexibility in another embodiment decreases where first tube section 20 is joined and overlapped with second tube section 42, at 44, but increases from first tube distal region distal portion 32 to second tube proximal region distal portion 60. Thus, in one embodiment, with a possible discontinuity at 44, flexibility increases distally over first tube section 20 and second tube section 42.

Referring now to FIG. 3, first tube section 20 is illustrated joined to second tube section 42. Proximally, first tube section 20 includes outer layer 36, a stiffening sleeve 38, and an inner layer 34. Proceeding distally, stiffening sleeve 38 terminates, thereby increasing flexibility, and outer layer 36 tapers and terminates, also increasing flexibility over the taper and distally beyond. Second tube section 42 has a flexibility where inner layer 46 and outer layer 48 are thickest, with the flexibility increasing distally over taper 50 in outer layer 48. Thus, through changes of materials and tapering layer thicknesses, the flexibility can increase gradually over a catheter's length.

Materials suitable for use with the present invention are preferably melt-processable, extrudable, and should be compatible so as to adhere to each other in the portions having multiple layers. Examples of materials believed suitable for use with the present invention include aliphatic and aromatic polyamides, polyamide copolymers, polyester, and polyester co-polymers. Specific polymers can include LCP, LCP polyester copolymers, polyetherimide, polyetheretherketone, polyvinyl chloride, polyimide, ARNITEL, polysulfone, or polyethersulfone. Further, polyether block amide (e.g., PEBAX) and CRISTAMID are believed to be suitable materials for forming layers according to the present invention. Materials suitable for formation of the stiffening sleeve include stainless steel and Nitinol wire. A tie layer (or special compatibilizing layer) may also be used between two normally incompatible structural resin layers in order to increase layer adhesion.

A semi-continuous co-extrusion process may be used to create the multiple, tapering and terminating tube section layers. One method uses an extruder having a co-extrusion head capable of having the feed to the outer layer turned off repeatedly with repeatable results. One single pass method uses two extrusion heads in line with each other, with the inner layer being extruded followed by the outer layer being extruded over the inner layer. A double pass method can use a single extrusion head, with the inner layer being extruded and cooled, followed by the outer layer being extruded over the inner layer, with different, preferably stiffer material being extruded during the second pass. One method includes extrusion over a core wire, with the later removal of that wire to create a smooth walled lumen having a constant inside diameter. Another method utilizes a shrink wrap material for the outer layer.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A multi-layer catheter tube section comprising:

a proximal double layer region and a distal single layer region;

a first tube having a wall thickness and formed of material having a first flexibility, said first tube extending from said proximal region to said distal region;

a second tube disposed over said first tube in said proximal region, said second tube formed of material having a second flexibility and having a wall thickness, said second tube having a taper with distally decreasing wall thickness in said catheter tube section proximal region, said taper having a length substantially greater than said first tube wall thickness, such that said catheter tube section has distally increasing flexibility; and a stiffening sleeve disposed between said first tube and said second tube in said proximal region, said stiffening sleeve terminating in a proximal portion of said proximal region, such that said proximal region has a stiffness greater than that of a distal portion of said proximal region not having said sleeve.

2. A multi-layer catheter tube section as recited in claim 1 wherein said second tube proximal region includes a proximal portion having substantially constant wall thickness and a distal portion having said taper.

3. A multi-layer catheter tube section as recited in claim 1 wherein said catheter tube distal region includes a proximal portion having said taper, said second tube terminating within said proximal portion.

4. A multi-layer catheter section as recited in claim 1 wherein said stiffening sleeve includes metal.

5. A multi-layer catheter section as recited in claim 1 wherein said stiffening sleeve includes metal wire.

6. A multi-layer catheter section as recited in claim 1 wherein said stiffening sleeve includes a wire braid.

7. A multi-layer catheter section as recited in claim 1 wherein said stiffening sleeve includes a wire helix.

8. A multi-layer catheter tube section as recited in claim 2 wherein said second tube distal region includes a proximal portion having said taper, said second tube terminating within said proximal portion.

9. A multi-layer catheter tube section as recited in claim 6 further comprising a stiffening sleeve in said proximal region, said stiffening sleeve terminating in said proximal portion of said proximal region, such that said proximal region proximal portion having said stiffening sleeve has a stiffness greater than that of a distal portion of said proximal region not having said sleeve.

10. A multi-layer catheter section as recited in claim 7 wherein said stiffening sleeve includes a wire braid.

11. A multi-layer catheter section as recited in claim 7 wherein said stiffening sleeve includes a wire helix.

12. A multi-layer catheter section comprising:

a proximal double layer region and a distal single layer region;

a first layer having a thickness and formed of a first material having a first flexibility, said first layer extending from said proximal region to said distal region;

a second layer disposed over said first layer in said proximal region, said second layer formed of a second material having a second flexibility and having a thickness, said second layer including a taper with said second layer thickness decreasing distally, said taper having a length substantially greater than said first layer thickness, such that said catheter tube section has distally increasing flexibility; and a stiffening sleeve disposed between said first layer and said second layer in said proximal region, such that said proximal region has a stiffness greater than that of said distal region.

13. A multi-layer catheter section as recited in claim 12 wherein said stiffening sleeve includes a wire braid.

14. A multi-layer catheter section as recited in claim 12 wherein said stiffening sleeve includes a wire helix.

* * * * *

UNITED STATES PATENT AND TRADEMARK OFFICE
CERTIFICATE OF CORRECTION

PATENT NO. : 6,045,547
DATED : April 4, 2000
INVENTOR(S) : Brooke Q. Ren et al.

It is certified that error appears in the above-identified patent and that said Letters Patent is hereby corrected as shown below:

Column 6,
Line 1, after the word claim, please delete "1" and insert therefor -- 4 --.

Signed and Sealed this

Eighteenth Day of September, 2001

Attest:

NICHOLAS P. GODICI
Attesting Officer  Acting Director of the United States Patent and Trademark Office